US009844389B2

(12) United States Patent
Van Andel

(10) Patent No.: US 9,844,389 B2
(45) Date of Patent: Dec. 19, 2017

(54) PUSH-TO-CLOSE ACTUATED DUAL ACTION SPACED PIVOT ASSEMBLY FOR SURGICAL INSTRUMENT JAWS, BLADES, AND FORCEPS

(71) Applicant: James A Van Andel, Walnut Grove, CA (US)

(72) Inventor: James A Van Andel, Walnut Grove, CA (US)

(73) Assignee: SCHOLTEN SURGICAL INSTRUMENTS, INC., Lodi, CA (US)

( * ) Notice: Subject to any disclaimer, the term of this patent is extended or adjusted under 35 U.S.C. 154(b) by 533 days.

(21) Appl. No.: 14/511,482

(22) Filed: Oct. 10, 2014

(65) Prior Publication Data

US 2016/0100851 A1 Apr. 14, 2016

(51) Int. Cl.
| | |
|---|---|
| *A61B 17/00* | (2006.01) |
| *A61B 17/29* | (2006.01) |
| *A61B 10/06* | (2006.01) |
| A61B 17/3201 | (2006.01) |
| A61B 17/295 | (2006.01) |

(52) U.S. Cl.
CPC ............ *A61B 17/29* (2013.01); *A61B 10/06* (2013.01); *A61B 17/295* (2013.01); *A61B 17/2909* (2013.01); *A61B 17/3201* (2013.01); *A61B 2017/2902* (2013.01); *A61B 2017/2903* (2013.01); *A61B 2017/2911* (2013.01); *A61B 2017/2912* (2013.01); *A61B 2017/2913* (2013.01); *A61B 2017/2916* (2013.01); *A61B 2017/2919* (2013.01); *A61B 2017/2926* (2013.01); *A61B 2017/2933* (2013.01)

(58) Field of Classification Search
CPC ..... A61B 10/06; A61B 17/29; A61B 17/2909; A61B 17/295; A61B 17/3201; A61B 2017/2902; A61B 2017/2903; A61B 2017/2911; A61B 2017/2912; A61B 2017/2913; A61B 2017/2916; A61B 2017/2919; A61B 2017/2926; A61B 2017/2932; A61B 2017/2933; A61B 2017/2936; A61B 2017/2939; A61B 2017/2944; A61B 2017/2947
See application file for complete search history.

(56) References Cited

U.S. PATENT DOCUMENTS 6,159,162 A * 12/2000 Kostylev ................ A61B 10/06
600/564

* cited by examiner

*Primary Examiner* — Robert Lynch

(57) ABSTRACT

A push-to-close actuated, dual-action, spaced pivot, assembly for jaws, blades, and forceps devices. The assembly is structured for use with a push rod, cable, or solid wire forceps actuator surgical instrument. A jaw receiving body of the assembly is adapted to receive a wide variety of types of jaws performing different surgical functions. Two separate moving jaws each pivot about a separate spaced pivot pin, on opposite sides of the jaw body centerline. A handle with a pushing actuating rod provides a pushing motion to a drive rod, cable, or solid wire within a cable sheath to push a connected yoke in the assembly to push against the jaws to close the jaws together.

12 Claims, 8 Drawing Sheets

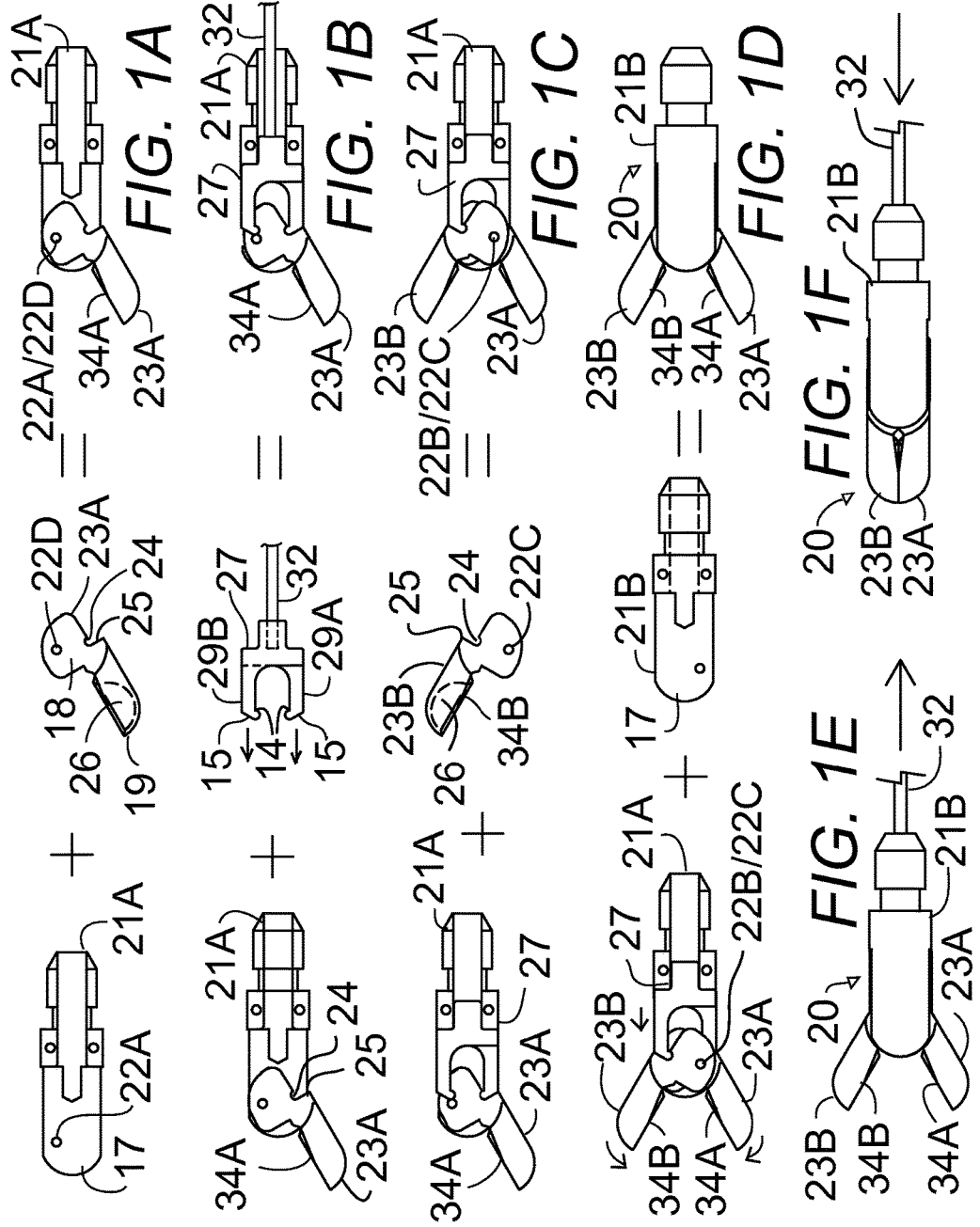

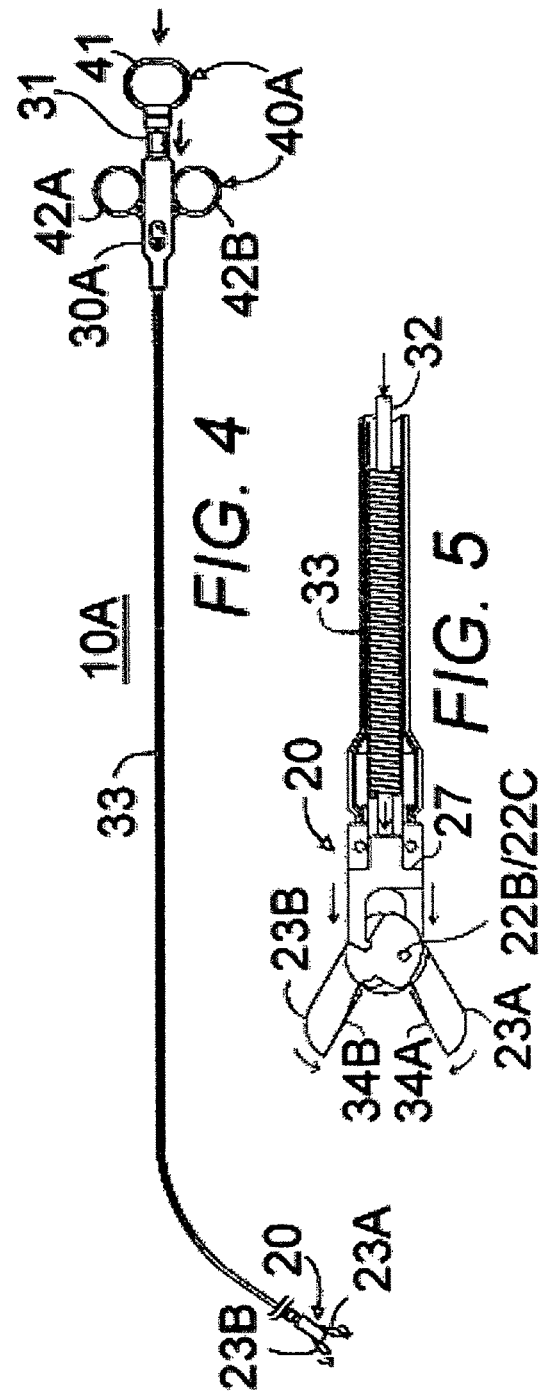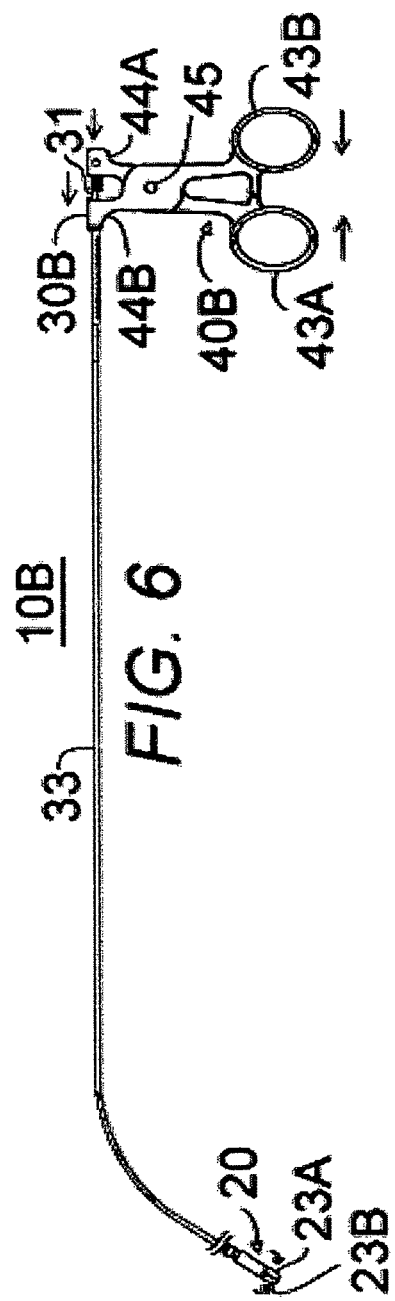

PUSH-TO-CLOSE ACTUATED DUAL ACTION SPACED PIVOT ASSEMBLY FOR SURGICAL INSTRUMENT JAWS, BLADES, AND FORCEPS

CROSS-REFERENCE TO RELATED APPLICATIONS

Not Applicable.

STATEMENT REGARDING FEDERALLY SPONSORED RESEARCH OR DEVELOPMENT

Not Applicable.

THE NAMES OF THE PARTIES TO A JOINT RESEARCH OR DEVELOPMENT

Not Applicable.

BACKGROUND OF THE INVENTION

Field of the Invention

The present invention relates to a forceps jaw assembly for a surgical instrument and in particular to a push-to-close actuated, dual-action, spaced pivot, assembly for jaws, blades, and forceps devices specifically structured for use with a push rod, cable, or solid wire forceps actuator and adapted for a wide variety of types of jaws including, but not limited to any type of grasping, cutting, clamping, holding, positioning, biopsying, and other types of jaws for surgical use; the instrument comprising a pair of interacting moving jaws for a dual jaw movement interacting jaw structure, each jaw having a unique structure configured for actuation by a pushing force against the two separate jaws on two spaced pivot fulcrum points, one for each jaw, on opposite sides of the centerline of a jaw retaining body, the two pivot points being at the furthest point possible away from each other while still maintaining a strong structure, so that the push drive force is applied by a jaw control yoke having opposing distal arms, one for each jaw, with a pushing head for each jaw to push a protruding hip having drive force point on the direct opposite side of the centerline from the fulcrum to close the jaws together, and by positioning the pivot point fulcrum and drive force point as far away from each other as the structure allows, the maximum crank angle at any point of the jaw actuation is produced, to maximize the force of the jaws with both jaws moving simultaneously, the yoke pushed by a driving cable and an actuation rod pushed by a handle mechanism which pushes the jaws together and a locking mechanism in a proximal control handle to hold the jaws together, each of the yoke arms further comprising a hook to hook a détente in a jaw, the yoke being pulled to pull open both jaws simultaneously.

Description of Related Art Including Information Disclosed Under 37 CFR 1.97 and 1.98

Most of the prior art dual-action biopsy or grasping jaw sets use a central common pivot pin for both jaws that is on the center line of the jaw body. These jaws, having a centerline pivot, limit the mechanical advantage applied to the grasping or cutting or other jaw action by limiting the crank arm distance available between the pivot points. Most other jaw sets, if not directly linked to the actuation wire use link arms to connect their center pivoting jaws to the actuation drive wire or mechanism. These mechanisms lose all or most mechanical advantage as the jaws close and the links, jaws, and actuation wire all line up on centerline, just when they need to provide the most force. Essentially they progressively lose mechanical advantage as they close.

U.S. Pat. No. 7,488,296, issued Feb. 10, 2009 to Van Andel, describes a plastic disposable scissor-action biopsy or grasping tool handle that has a standard adapter tube attached to a front arm of the handle. An actuator rod attaches to the handle with the standard biopsy tool driver cable attached to the actuator rod. An actuator rod front tubular portion is slideable within the front handle arm. The actuator rod back portion has an elongated horizontal slot through it, having a stop pin through the slot attached to a pair of mating stop pin holes within an actuator rod receiving recess in the back arm of the handle. A spring interacts between an actuator rod spring stop and the rear handle arm to regulate bite pressure of the biopsy cutting tool. The back handle arm pushes the driver cable to operate the biopsy cutting tool.

U.S. Pat. No. 4,815,476, issued Mar. 28, 1989 to Clossick, shows a biopsy forceps device that comprises a handle portion an elongate flexible hollow body portion having a proximal end coupled to the handle portion and a distal end. A forceps assembly is coupled to the distal end and includes a pair of forceps. A stylet control wire in the body portion is coupled to the pair of forceps at the distal end of the body portion. A locking hub assembly is coupled between the handle portion and the proximal end of the body around the stylet/control wire and includes a locking hub and locking means for locking the stylet/control wire in an axial position thereof to the locking hub assembly relative to the body portion upon rotation of the locking hub.

U.S. Pat. No. 5,171,258, issued Dec. 15, 1992 to Bales, et al., claims double acting, dual pivot disposable laparoscopic surgical instruments. Disposable laparoscopic surgical instruments for insertion through trocar tubes are disclosed. The instruments broadly include: a hollow aluminum tube; an aluminum clevis which is formed separately from the aluminum tube with the distal end of the hollow aluminum tube crimped around the proximal end of the clevis, and with the clevis including an axially off-set pivot pin; at least one end effector element having a pivot hole through which the off-set pivot pin of the clevis is pivotally engaged, and another through-hole; an aluminum push rod extending at least partially through the hollow aluminum tube and mechanically coupled to the end effector element; and apparatus for imparting reciprocal motion to the push rod relative to the aluminum tube, whereby the reciprocal motion is translated at an offset pivot of the clevis into a high torque pivotal motion of the end effector element.

U.S. Pat. No. 5,308,358, issued May 3, 1994 to Bond, shows rigid-shaft surgical instruments that can be disassembled for improved cleaning The invention relates to single-tool surgical instruments, such as scissors or forceps which do not pass through a channel in an operating laparoscope, which contain moving actuator parts at the end of a long slender shaft comprising a tube and a yoke. The actuator is operated by means of a handle assembly, which either forces or retracts an interior rod through a hollow shaft tube. These instruments can be disassembled to remove the interior rod from inside the shaft tube. This allows improved cleaning and removal of blood or tissue residues from the interior rod and shaft tube prior to sterilization, to provide for more effective and reliable sterilization of the components. The assembly includes a union coupling near the handle which allows the shaft tube to be disengaged from the handle without rotating either the interior rod or the shaft tube. After the shaft tube has been disengaged and pulled away slightly, the shaft and actuator assembly are rotated relative to the handle assembly. This unscrews the actuator assembly from the end of the interior rod. After the interior rod disengages from the actuator assembly, the shaft and actuator are pulled away from the handle assembly and interior rod. This exposes the interior rod and provides open access to the interior of the shaft tube, so that both components can be cleaned to remove any blood or tissue residue prior to sterilization. If desired, the actuator assembly can be removed from the end of the shaft tube, by removing a pivot screw, or by installing the actuator assembly in a shaft yoke device which can be removed from the end of the shaft tube.

U.S. Pat. No. 5,263,967, issued Nov. 23, 1993 to Lyons, III, et al., is for a medical instrument including a tubular extension within which and to which two movable end effectors, such as jaw members, are rotatably attached by a pivot. The proximal end of each end effector is pivotally attached to and butts against a drive surface of its respective arm of a dual action drive member also located within the tubular extension. As the dual action drive member is moved proximally or distally within the tubular extension, the distal ends of the end effectors rotate or counter rotate about the pivot in opposition to one another. The dual action drive member paired arms have end surfaces which transfer, to the end effectors, the force required to rotate the end effectors toward one another, thereby reducing the shear force applied to pivot posts on the arms used to open the jaws. The dual action drive member may be used with a variety of different end effector devices including but not limited to medical grippers, hole punches, dissectors, extractors, scissors, and clamps.

U.S. Pat. No. 6,818,007, issued Nov. 16, 2004 to Dampney, et al., describes an effector comprising a pair of opposing jaws directly mounted on a keeper so that the jaws are pivotable about the keeper. The jaws are connected to an actuating member within the keeper, so that translational movement of the actuating member causes the jaws between an open and closed position.

U.S. Pat. No. 7,186,261, issued Mar. 6, 2007 to Prestel, provides a medical forceps with a tubular outer shank, on whose distal end there is formed a forceps jaw with two jaw parts. The two jaw parts are each rotatably mounted on the outer shank at two sides opposite one another. A tubular inner shank for actuating the jaw parts is displaceably arranged in the inside of the outer shank in its longitudinal direction. The inner shank is coupled to the two jaw parts for their actuation via two lever systems. Each of the lever systems is linked to the two jaw parts, one lever system on each of the two opposite sides U.S. Patent Application No. 20130131544, published May 23, 2013 by Bowden, Mark A., et al., claims improved biopsy forceps which include pivotally coupled self aligning jaws with drainage holes therethrough. The biopsy forceps include a pair of jaw members that include cup shaped jaws. The biopsy forces may be formed by a series of metal etching and forming operations to allow the manufacture of the biopsy forceps using high volume manufacturing techniques.

What is needed is a push-to-close actuated, dual-action, spaced pivot, assembly for jaws, blades, and forceps devices specifically structured for use with a push rod, cable, or solid wire forceps actuator and adapted for a wide variety of types of jaws, the assembly having two interacting moving jaws for a dual jaw movement interacting jaw structure configured for actuation by a pushing force against the two separate jaws simultaneously about two separate spaced pivot fulcrum points, one for each jaw, on opposite sides of the centerline, the two pivot points being at the furthest point possible away from each other while still maintaining a strong structure, so that the push drive force is applied to a drive force point on the direct opposite side of the centerline from the fulcrum, and by positioning the pivot point fulcrum and drive force point as far away from each other as the structure allows, the maximum crank angle at any point of the jaw actuation is produced to maximize the force of the jaws with both jaws moving together to operate.

BRIEF SUMMARY OF THE INVENTION

An object of the present invention is to provide a push-to-close actuated, dual-action, spaced pivot, assembly for jaws, blades, and forceps devices specifically structured for use with a push rod, cable, or solid wire forceps actuator and adapted for a wide variety of types of jaws, the assembly having two interacting moving jaws for a dual jaw movement interacting jaw structure configured for actuation by a pushing force against the two separate jaws simultaneously about two separate spaced pivot fulcrum points, one for each jaw, on opposite sides of the centerline, the two pivot points being at the furthest point possible away from each other while still maintaining a strong structure, so that the push drive force is applied to a drive force point on the direct opposite side of the centerline from the fulcrum, and by positioning the pivot point fulcrum and drive force point as far away from each other as the structure allows, the maximum crank angle at any point of the jaw actuation is produced to maximize the force of the jaws with both jaws moving together to operate with maximum force.

A corollary object of the present invention is to provide a push-to-close actuated dual-action spaced pivot jaws forceps assembly adapted for a wide variety of pairs of jaws including, but not limited to any type of grasping, cutting, clamping, holding, positioning, biopsying, and other types of jaws for surgical use and in particular for a combined function biopsy forceps and grasper instrument dual-action jaw specifically structured and actuated for heart biopsy which can be used for any type of tissue biopsy, the instrument comprising a surgical instrument jaws forceps assembly having interacting moving jaws for a cutting and grasping dual jaw movement interacting jaw structure each jaw having a collecting bowl with a sharp cutting edge that, by its unique geometry configured for actuation by a pushing force against the two separate jaws simultaneously about two separate spaced pivot fulcrum points, one for each jaw, on opposite sides of the centerline, the two pivot points being at the furthest point possible away from each other while still maintaining a strong structure, so that the push drive force is applied to a drive force point on the direct opposite side of the centerline from the fulcrum, and by positioning the pivot point fulcrum and drive force point as far away from each other as the structure allows, the maximum crank angle at any point of the jaw actuation is produced to maximize the cutting and grasping force of the jaws with both jaws moving together to cut and grasp the tissue, the jaws pushed by a dual armed yoke attached to a drive cable, a drive rod, or a solid wire drive and an actuation pin pushed by a handle mechanism which pushes the jaws together, cutting and grasping the tissue and which handle mechanism locks to hold the jaws together to retain the tissue in the combined space formed by the two bowls of the jaws for removing the tissue from the patient.

A corollary object of the present invention is to provide a pair of dual action jaws driven by a forward pushing mechanism that overcomes all problems inherent in the prior art devices, wherein a push forward actuator is particularly suited for biopsies or grasping of moving organs such as hearts and lungs to produce a simple, safe and reliable device.

In brief, the present invention provides a push-to-close actuated, dual-action, spaced pivot, assembly for jaws, blades, and forceps devices specifically structured for use with a push rod, cable, or solid wire forceps actuator and adapted for a wide variety of types of jaws. Two separate moving opposing jaws each pivot about a separate spaced pivot pin. In one embodiment, each opposing jaw has a collecting bowl having a sharp cutting edge so that the jaws pivot together to cut the tissue and mate together to collect the tissue in the combined bowl space. A handle with a pushing actuating pin provides a pushing motion against the jaws to close the jaws together. A handle locking mechanism locks the jaws together for holding the tissue to remove the jaws from the patient.

The dual-action (both jaws moving) cutting or grasping jaws with maximum jaw force leverage has two pivot fulcrum points, one for each jaw, on opposite sides of the jaw body centerline from the distal ends of the jaws. These two pivot points are at the furthest point possible away from each other while still maintaining a strong structure. The drive force for each jaw is applied to a drive force point on the direct opposite side of the centerline from the fulcrum. By positioning the pivot point fulcrum and drive force point as far away from each other as the structure allows, the maximum crank angle is produced at any point of the jaw actuation.

An advantage of the present invention is that it provides a two movable jaw structure that by its unique geometry with dual spaced pivot points to maximize the cutting, gripping, or other force being applied in a medical procedure.

An additional advantage of one embodiment of the jaws of the present invention is that it provides a collection bowl assembly in the movable jaw cutting structures to both cut and contain tissue.

Another advantage of the present invention is that it provides a control handle structure with a syringe-type actuator that pushes the actuator pin and consequently the drive cable or drive rod or drive solid wire for extra power and provides a unique lateral actuator rod motion locking mechanism or a control handle with a scissors-type actuator providing a push-to-close action and an alternate locking mechanism.

An added advantage of the present invention is that it provides two movable jaw cutting structures that move simultaneously in an opposing manner.

BRIEF DESCRIPTION OF THE SEVERAL VIEWS OF THE DRAWINGS

These and other details of the present invention will be described in connection with the accompanying drawings, which are furnished only by way of illustration and not in limitation of the invention, and in which drawings:

FIG. 1A is a composite top plan view of the jaw body bottom plus a left jaw, using an example of a combined biopsy forceps and grasper instrument jaw for heart tissue biopsy and general body tissue biopsy, showing the left jaw and body bottom individually and then assembled together;

FIG. 1B is a composite top plan view of the combined jaw body bottom and left jaw of FIG. 1A plus the yoke individually and then assembled together;

FIG. 1C is a composite top plan view of the combined jaw body bottom, left jaw, and yoke of FIG. 1B plus the right jaw individually and then assembled together;

FIG. 1D is a composite top plan view of the combined jaw body bottom, left jaw, yoke, and right jaw of FIG. 1C plus the jaw body top individually and then assembled together;

FIG. 1E is a s top plan view of the combined jaw body bottom, left jaw, yoke, right jaw, and jaw body top of FIG. 1D showing the drive cable pulling the yoke to open the jaws;

FIG. 1F is a top plan view of the combined jaw body bottom, left jaw, yoke, right jaw, and jaw body top of FIG. 1D showing the drive cable pushing the yoke to close the jaws to cut through and contain tissue sample for removal from the body;

FIG. 4 is a side elevational view of the biopsy jaw device of the present invention used on a push-to-close activated syringe-type control handle, showing the combined biopsy forceps and grasper instrument jaws for heart tissue biopsy and general body tissue biopsy, with the jaws in the open position;

FIG. 5 is a top plan view in partial section showing the connection structure of the cable with the jaw assembly;

FIG. 6 is a side elevational view of the biopsy jaw device of the present invention used on a push-to-close activated scissor-type control handle, showing the combined biopsy forceps and grasper instrument jaws for heart tissue biopsy and general body tissue biopsy, with the jaws in the closed position;

DETAILED DESCRIPTION OF THE INVENTION

Figure 2A:
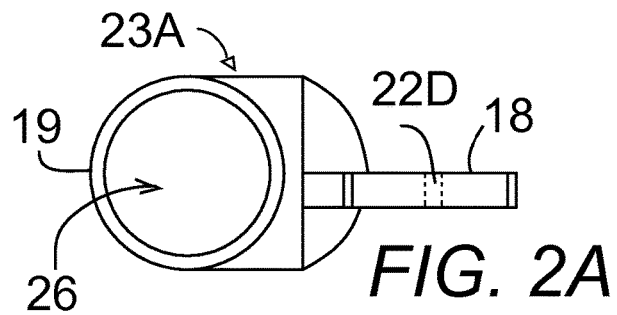
FIG. 2A is a side elevational view of the left jaw of the combined biopsy forceps and grasper instrument jaw device for heart tissue biopsy and general body tissue biopsy of the present invention, a pair of the combined biopsy forceps and grasper instrument jaw configured to cut through and contain tissue sample for removal from the body.
Figure 2B:
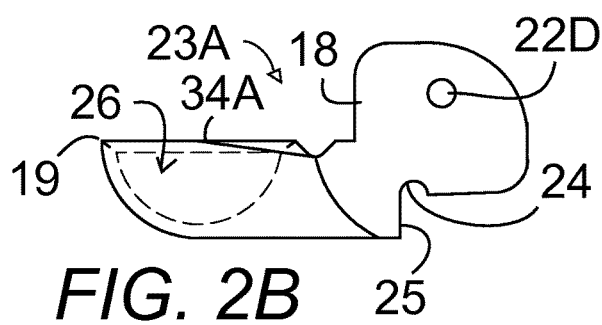
FIG. 2B is a top plan view of the left jaw of FIG. 2.
Figure 2C:
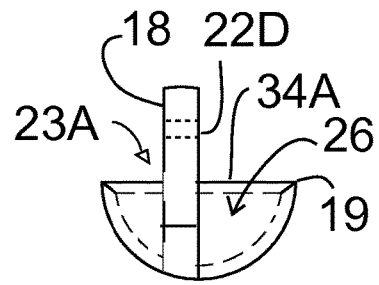
FIG. 2C is a proximal end elevational view of the left jaw of FIG. 2.
Figure 3A:
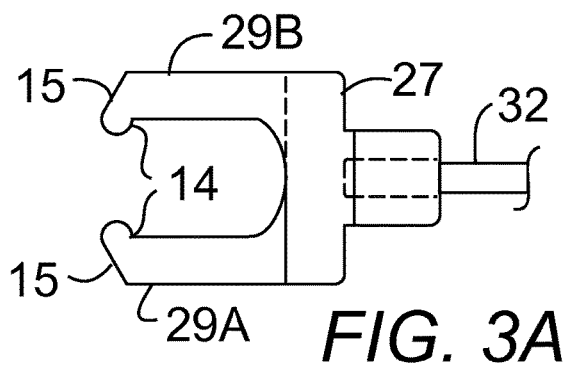
FIG. 3A is a top plan view of the yoke of the present invention, showing the two rigid spaced parallel arms extending from the distal end of the yoke body each having a pushing end for pushing a hip of one of the pair of jaws for closing the pair of jaws simultaneously and each having a hook to engage a détente on one of the pair of jaws to enable both hooks to pull the détentes simultaneously to open the jaws, and the attached cable or rod or solid wire for pushing and pulling the yoke.
Figures 3B, 3C, 3D:
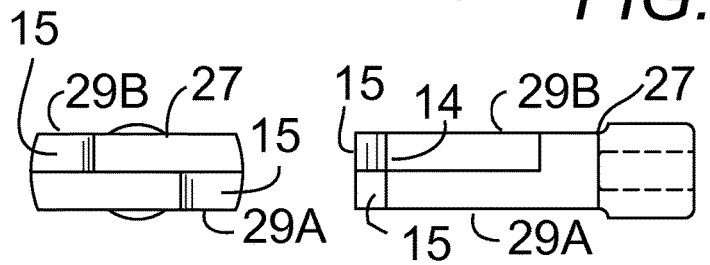
FIG. 3B is a distal end elevational view of the yoke of FIG. 3A, showing the pushing ends of the arms extending at different heights.
FIG. 3C is a side elevational view of the yoke of FIG. 3A, showing the arms extending from the yoke body at different heights.
FIG. 3D is a proximal end elevational view of the yoke of FIG. 3A, showing the opening for the cable or rod or solid wire to attach to the yoke body.

In FIGS. 1-21, a push-to-close actuated dual-action spaced assembly device 20 for jaws, blades, and forceps devices is specifically structured for use with a push actuated drive rod 32 or drive cable, or drive solid wire in a forceps actuator surgical instrument 10A and 10B adapted for a wide variety of types of jaws 23A and 23B, 53A and 53B, 63A and 63B, 73A and 73B, 83A and 83B, 93A and 93B.

In FIGS. 1A-1F, the device comprises a jaw retaining body 21A and 21B attached to a distal end of a push-to-close forceps actuator surgical instrument 10A and 10B, as shown in FIGS. 4 and 6. The jaw retaining body 21A and 21B comprising a jaw receiving platform 17 having a perpendicular protruding right pivot pin 22A on a first face of the jaw receiving platform spaced apart from a longitudinal center axis of the jaw receiving platform adjacent to a right edge of the jaw receiving platform and a perpendicular protruding left pivot pin 22B on a second face of the jaw receiving platform spaced apart from a longitudinal center axis of the jaw receiving platform adjacent to a left edge of the jaw receiving platform, thereby providing spaced pivot pins 22A and 22B.

In FIGS. 1A-1F and 2A-2C, two opposing moving jaws, a left jaw 23A and a right jaw 23B, each pivot about one of the separate spaced pivot pins 22A and 22B (respectively). Each of the jaws 23A and 23B comprising one of a pair of push-to-close actuated, dual-action, spaced pivot jaws on the distal end of the push-to-close forceps actuator surgical instrument, 10A and 10B, so that a left jaw 23A is pivotally connected to the right pivot pin 22A on the jaw retaining body and a right jaw 23B is pivotally connected to the left pivot pin 22B on the jaw receiving platform 17. Each of the jaws further comprising an exposed hip 25 on a proximal end of each of the jaws, spaced apart from each of the respective pivot pins 22A and 22B, for receiving a pushing force on each of the exposed hips 25 simultaneously to pivot the distal ends of the pair of jaws together for performing a surgical function.

By positioning the pivot point fulcrum, pivot pins 22A and 22B, and drive force point, the exposed hips 25, as far away from each other as the structure allows, the maximum crank angle at any point of the jaw actuation is produced to maximize the force of the jaws with both jaws 23A and 23B moving together to operate with maximum force.

The distal ends of the pair of jaws comprise a mating pair of structured surgical elements 34A and 34B configured to mate together to perform at least one surgical function when the pair of jaws 23A and 23B are pivoted together, as shown in FIG. 1F. Each of the jaws has a détente 24 adjacent to each of the exposed hips 25 for receiving a pulling force to pull the pair of jaws 23A and 23B apart, as shown in FIG. 1E. Each of the pair of jaws has a pivot pin opening 22D and 22C in a proximal end 18 to removably receive one of the spaced pivot pins 22A and 22B respectively, for attaching each of the jaws 23A and 23B to the jaw retaining body 21A and 21B so that different jaw sets having mating pairs of structured surgical elements to accomplish different surgical functions can be installed by the manufacturer on the same jaw retaining body: jaws 23A and 23B having surgical elements 34A and 34B (in FIGS. 1 and 2), jaws 53A and 53B having surgical elements 54A and 54B (in FIGS. 7-9), jaws 63A and 63B having surgical elements 64B and 64B (in FIGS. 10-12), jaws 73A and 73B having surgical elements 74A and 74B (in FIGS. 13-15), jaws 83A and 83B having surgical elements 84A and 84B (in FIGS. 16-18), jaws 93A and 93B having surgical elements 94A and 94B (in FIGS. 19-21), as well as any other types of jaws having the same proximal configuration for mounting on the distal end of the push-to-close forceps actuator surgical instrument 10A and 10B.

In FIGS. 1B-1D and FIGS. 3A-3D, a yoke 27 to open and close the pair of jaws 23A and 23B is operated by a drive cable 32, which could alternately be a drive rod or a solid wire drive from a control handle 30A and 30B on a proximal end of the push-to-close forceps actuator surgical instrument 10A and 10B, as shown in FIGS. 4 and 6. The yoke 27 comprises a rigid yoke body 27 attached to the drive cable 32, drive rod, or solid wire drive at a proximal end of the yoke body. At a distal end of the yoke body, two rigid spaced parallel arms 29A and 29B rigidly extend from the distal end of the yoke body for operating the jaws 23A and 23B. The spaced arms 29A and 29B each comprise a pushing end 15 in contact with one of the exposed hips 25 of one of the pair of jaws 23A and 23B to enable the pair of arms 29A and 29B to push both of the exposed hips 25 of the pair of jaws simultaneously, pushed by the drive cable 32, drive rod, or solid wire drive, pivoting the distal ends with facing surgical elements 34A and 34B of the pair of jaws together, as shown in FIG. 1F, to perform a surgical function. The spaced arms 29A and 29B each further comprise a hook 14 to engage one of the détentes 24 of one of the pair of jaws to enable both hooks 14 to pull the détentes 24 simultaneously, pulled by the drive cable 32, drive rod, or solid wire drive, to pivot the distal ends of the pair of jaws open as shown in FIG. 1E.

In FIGS. 4-6, the drive cable 32, drive rod, or drive solid wire performs a pushing and pulling drive motion within a cable sheath 33 extending between the jaw retaining body 20 and the control handle 30A or 30B. The control handle 30A or 30B is held by a medical professional and has means for controlling the drive cable 32, drive rod, or solid wire drive to push the drive cable, drive rod, or solid wire drive to close the jaws 23A and 23B, as shown in FIG. 6, and to pull the drive cable 32 to open the jaws 23A and 23B, as shown in FIG. 4, thereby providing a push-to-close actuated dual-action spaced pivot jaws assembly 20 specifically structured for use with a push-to-close rod, cable, or solid wire actuator surgical instrument 10A and 10B adapted for a wide variety of types of jaws performing different surgical functions.

In FIGS. 4-6 the drive rod 32, drive cable or drive solid wire are movably housed within a rigid or flexible cable sheath housing 33 with an actuator pin 31 connected to a distal end of the drive rod 32, drive cable or drive solid wire. The actuator pin 31 slides axially within the control handle 30A and 30B, and further comprises a means for manually controlling the actuator pin 31 with the pin extending beyond the control handle 30A and 30B.

In FIGS. 1-2 and 4-21 a variety of pairs of jaws 23A and 23B (in FIGS. 1 and 2), 53A and 53B (in FIGS.7-9), 63A and 63B (in FIGS. 10-12), 73A and 73B (in FIGS. 13-15), 83A and 83B (in FIGS. 16-18), 93A and 93B (in FIGS. 19-21), a each has different mating pairs of structured surgical elements 23A and 23B having surgical elements 34A and 34B (in FIGS. 1 and 2), jaws 53A and 53B having surgical elements 54A and 54B (in FIGS.7-9), jaws 63A and 63B having surgical elements 64B and 64B (in FIGS. 10-12), jaws 73A and 73B having surgical elements 74A and 74B (in FIGS. 13-15), jaws 83A and 83B having surgical elements 84A and 84B (in FIGS. 16-18), jaws 93A and 93B having surgical elements 94A and 94B (in FIGS. 19-21), configured to perform at least one different surgical function. These may comprise structured surgical elements taken from the list of structured surgical elements consisting of biopsy collecting elements, biopsy cutting and collecting elements, tissue cutting and removing elements, heart tissue biopsy collecting elements, body tissue biopsy collecting elements, body tissue sample cutting and containing and removing elements, holding elements, positioning elements, manipulating elements, grasping elements, traumatic grasping elements, grasping and manipulating elements, grasping and dissecting elements, atraumatic grasping elements, atraumatic grasping and dissecting elements, atraumatic soft tissue grasping and dissecting elements, soft tissue grasping and manipulation elements, soft tissue grasping and pulling elements, cutting elements, tissue cutting elements, tissue and suture material cutting elements, clamping elements, foreign body grasping elements, surgical elements, jaw type elements.

In FIGS. 1A-1F and 2A-2C, a heart biopsy collecting embodiment of the present invention comprises two opposing moving jaws 23A and 23B each pivot about a separate spaced pivot pin 22A and 22B (respectively). Each of the jaws 23A and 23B comprises a biopsy capture bowl 26 on a distal end for grasping, cutting, and containing biopsy tissue and a surrounding rim formed into a sharp cutting edge 19 for cutting tissue that is structured to cut and mate with the opposing jaw cutting edge 19 and biopsy capture bowl 26 in a plane aligned with the longitudinal center axis of the jaw receiving platform 17 and perpendicular to the jaw receiving platform 17 of the jaw, retaining body 21A and 21B. The jaws 23A and 23B cut and collect biopsy tissue in the combined biopsy capture bowl 26. Each of the jaws 23A and 23B pivotally attached to a separate pivoting pin 22A and 22B on the jaw receiving platform 17 and each of the jaws 23A and 23B pushed together simultaneously by the yoke 27 to cut and collect biopsy tissue and remove it from the body to be studied after releasing the biopsy tissue by having the yoke 27 pull the jaws 23A and 23B apart after removal from the body, thereby providing a combined biopsy forceps and grasper instrument jaw device for heart tissue biopsy and general body tissue biopsy.

Figure 7:
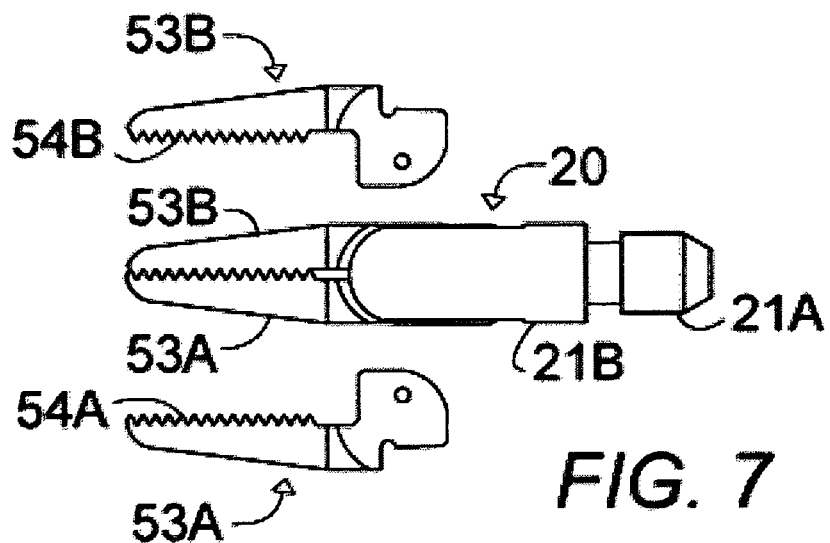
FIG. 7 is a composite top plan view of a pair of alligator jaws shown separately and mounted in a closed jaw position on a jaw retaining body, the interconnecting teeth of the jaws configured for atraumatic grasping and dissecting of delicate soft tissue and alternately for grasping a foreign body.
Figure 8:
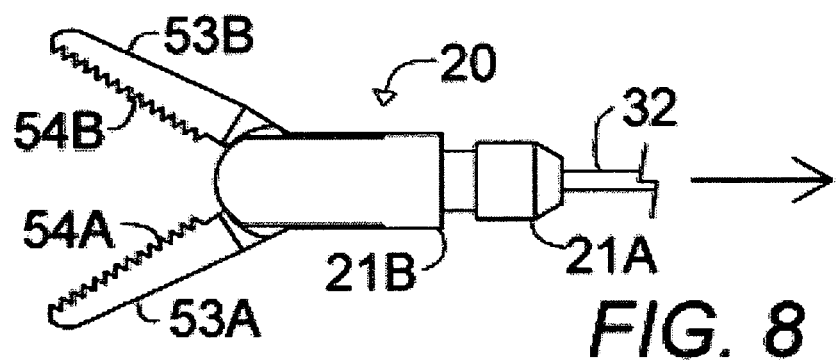
FIG. 8 is a top plan view of the pair of alligator jaws mounted on a jaw retaining body of FIG. 7, showing the jaws in an open position with the control cable pulling the jaws open.
Figure 9:
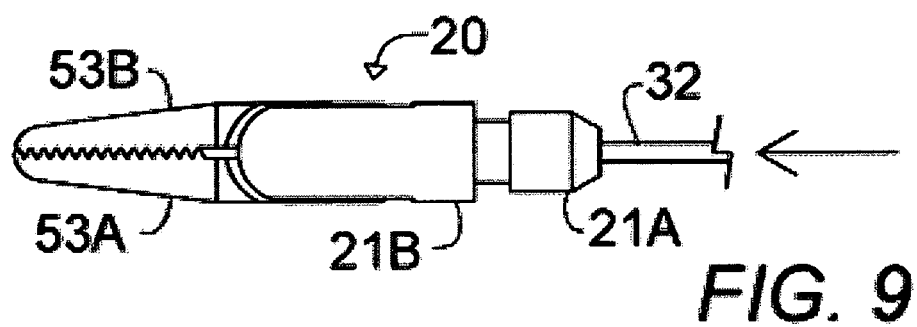
FIG. 9 is a top plan view of the pair of alligator jaws mounted on a jaw retaining body of FIG. 7, showing the jaws in a closed position with the control cable pushing the jaws closed.

In FIGS. 7-9, an alternate pair of jaws 53A and 53B comprises a pair of alligator jaws, each jaw comprising a distal end structure having triangular teeth 54A and 54B along the length of an interior inside mating edge of the distal end interconnecting with a similar array of triangular teeth on the other jaw of the pair of alligator jaws, the interconnecting teeth of the pair of alligator jaws configured for atraumatic grasping and dissecting of delicate soft tissue and alternately for grasping a foreign body.

Figure 10:
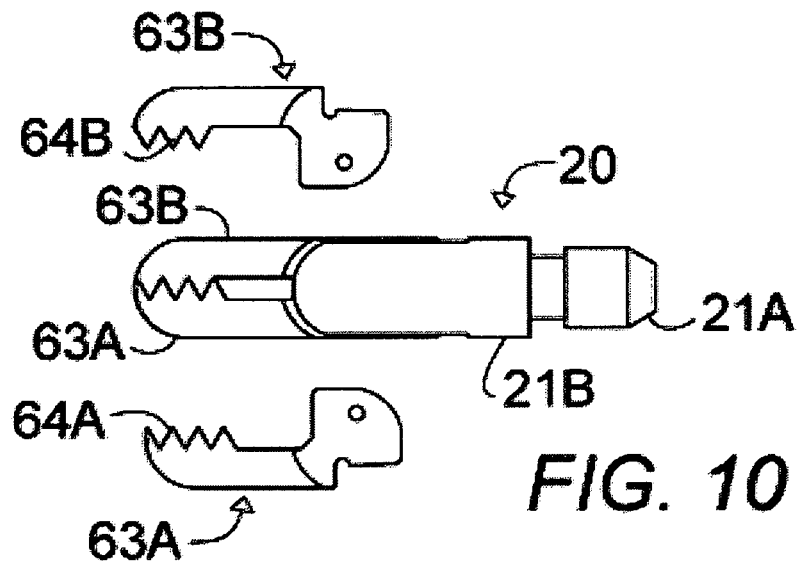
FIG. 10 is a composite top plan view of a pair of traumatic grasper jaws shown separately and mounted in a closed jaw position on a jaw retaining body, the partial distal array of large interconnecting teeth of the jaws configured to securely grasp and manipulate soft tissue and alternately to grasp a foreign body.
Figure 11:
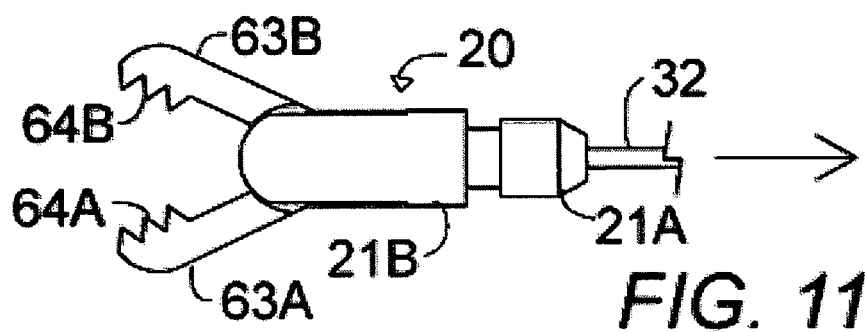
FIG. 11 is a top plan view of the pair of traumatic grasper jaws mounted on a jaw retaining body of FIG. 10, showing the jaws in an open position with the control cable pulling the jaws open.
Figure 12:
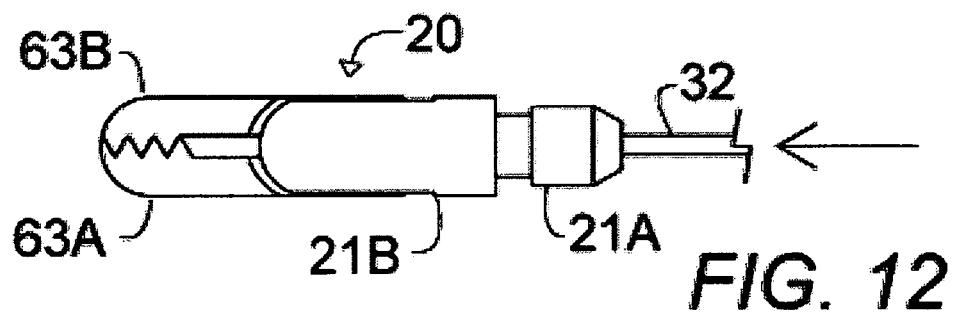
FIG. 12 is a top plan view of the pair of traumatic grasper jaws mounted on a jaw retaining body of FIG. 10, showing the jaws in a closed position with the control cable pushing the jaws closed.

In FIGS. 10-12 another alternate pair of jaws 63A and 63B comprises a pair of traumatic grasper jaws, each jaw comprising a distal end interior edge structure having a partial far end distal array of large isosceles shaped triangular teeth 64A and 64B interconnecting with a similar array of large triangular teeth on the far distal end of the other jaw, the traumatic grasper jaws configured to securely grasp and manipulate soft tissue and alternately to grasp a foreign body.

Figure 13:
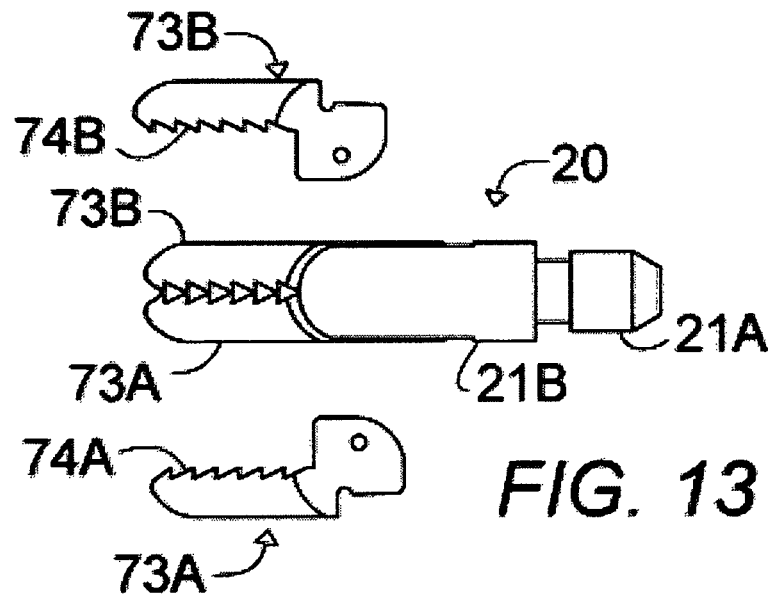
FIG. 13 is a composite top plan view of a pair of reverse tooth jaws, having a full array of teeth gripping edges perpendicular to the jaw and facing toward the back of the jaw, the reverse tooth jaws shown separately and mounted in a closed jaw position with only the points of the teeth of the two jaws in contact on a jaw retaining body, the full array of backwardly facing teeth of the jaws configured to securely grasp and manipulate soft tissue and specifically suited for grasping and pulling forces on soft tissue or foreign bodies.
Figure 14:
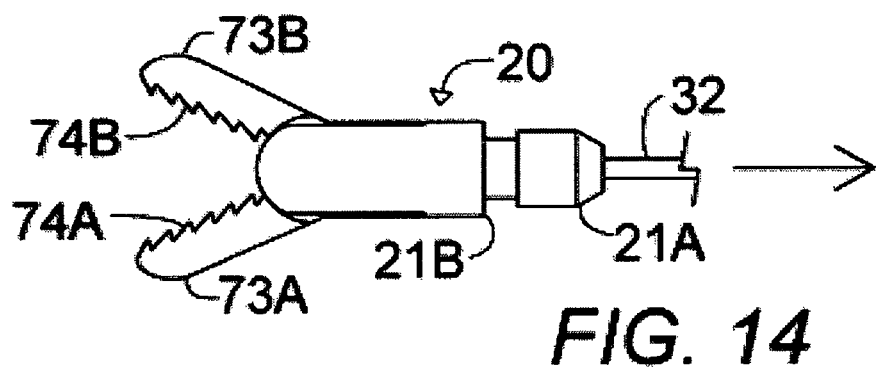
FIG. 14 is a top plan view of the pair of reverse tooth jaws mounted on a jaw retaining body of FIG. 13, showing the jaws in an open position with the control cable pulling the jaws open.
Figure 15:
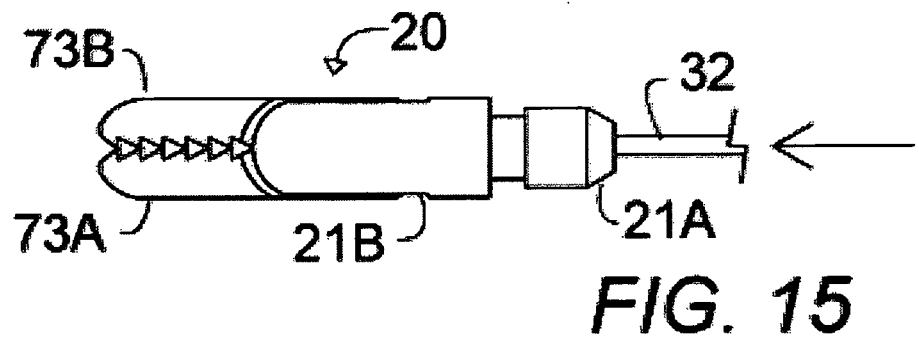
FIG. 15 is a top plan view of the pair of pair of reverse tooth jaws mounted on a jaw retaining body of FIG. 13, showing the jaws in a closed position with the control cable pushing the jaws closed.

In FIGS. 13-15, another alternate pair of jaws 73A and 73B comprises a pair of reverse tooth jaws, the interior edge of each jaw having a full array of right triangle shaped teeth having back-facing straight grasping edges 74A and 74B perpendicular to the jaw touching an array of tips of a similar array of teeth on the other blade, the reverse tooth jaws configured to securely grasp and manipulate soft tissue and specifically suited for grasping and pulling forces on soft tissue and foreign bodies.

Figure 16:
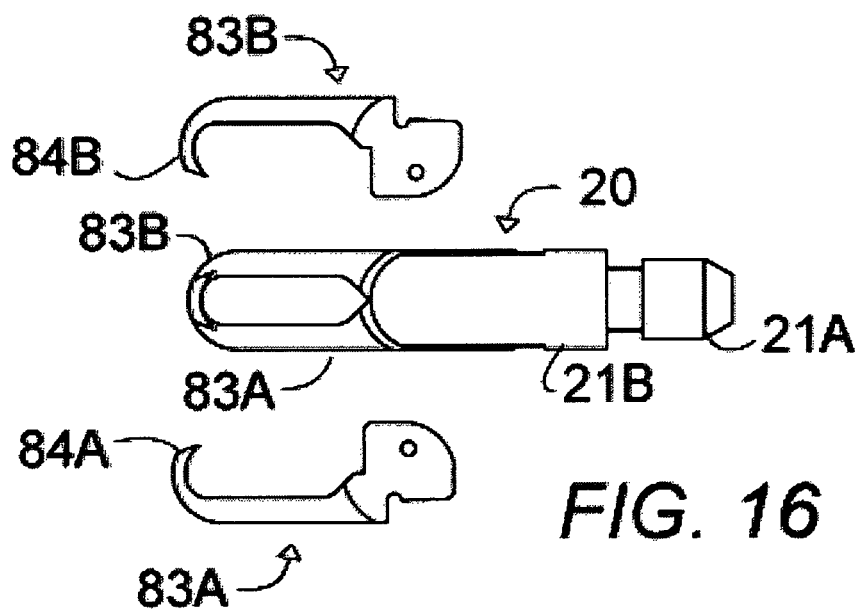
FIG. 16 is a composite top plan view of a pair of rat tooth jaws shown separately and mounted in a closed jaw position on a jaw retaining body, the overlapping distal end rearwardly facing pointed hook ends and cutting edges of the jaws configured to securely grasp, puncture, and manipulate soft tissue and specifically suited for grasping and pulling forces on soft tissue or foreign bodies.
Figure 17:
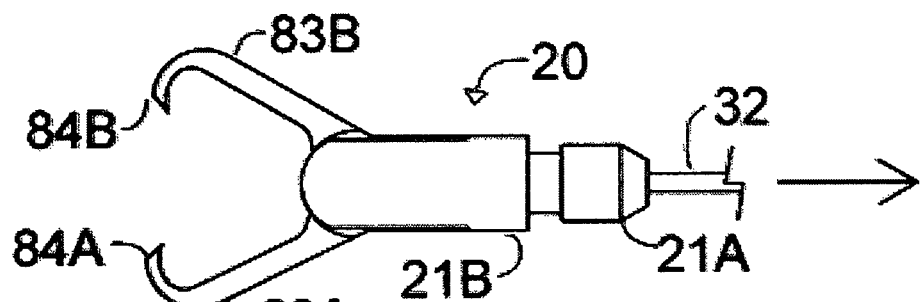
FIG. 17 is a top plan view of the pair of rat tooth jaws mounted on a jaw retaining body of FIG. 16, showing the jaws in an open position with the control cable pulling the jaws open.
Figure 18:
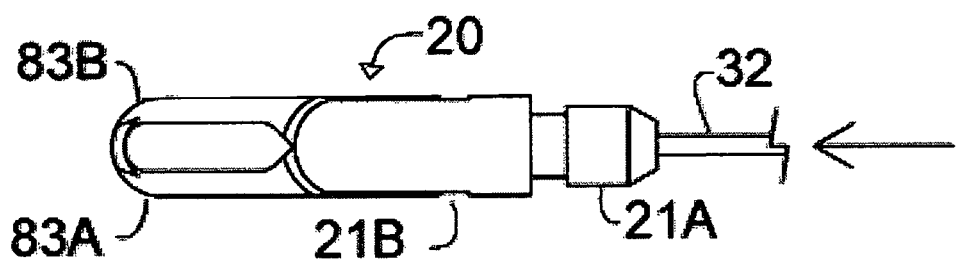
FIG. 18 is a top plan view of the pair of rat tooth jaws mounted on a jaw retaining body of FIG. 16, showing the jaws in a closed position with the control cable pushing the jaws closed.

In FIGS. 16-18, another alternate pair of jaws 83A and 83B comprises a pair of rat tooth jaws each jaw comprising an inwardly and rearwardly pointing cutting hook 84A and 84B on a far distal end overlapping with a similar rearwardly facing pointed cutting hook on the other rat tooth jaw, the rat tooth jaws configured to securely grasp, puncture, and manipulate soft tissue and specifically suited for grasping and pulling forces on soft tissue and foreign bodies.

Figure 19:
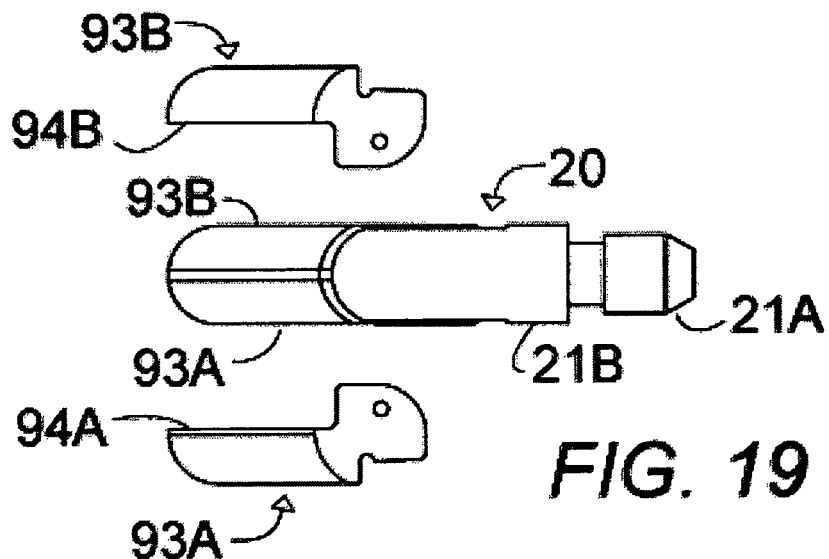
FIG. 19 is a composite top plan view of a pair of scissors jaws, having a full length interacting cutting edge on the facing edges of each blade to cut like scissors, the scissors jaws shown separately and mounted in a closed jaw position with the full length scissors edges interacting on a jaw retaining body, the scissors jaws configured to cut soft tissue as well as suture material.
Figure 20:
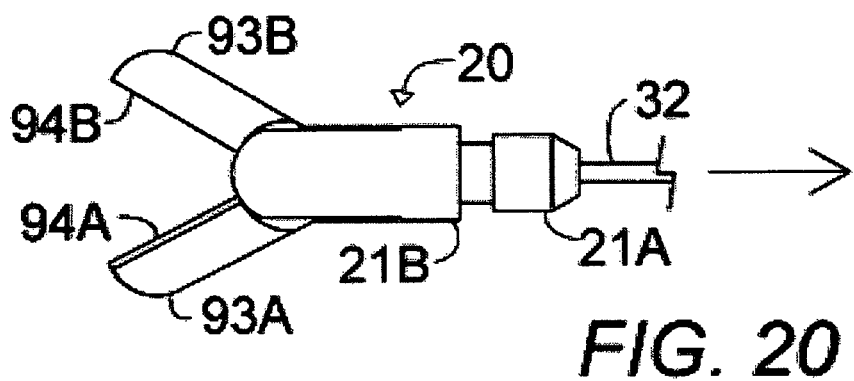
FIG. 20 is a top plan view of the pair of scissors jaws mounted on a jaw retaining body of FIG. 19, showing the jaws in an open position with the control cable pulling the jaws open.
Figure 21:
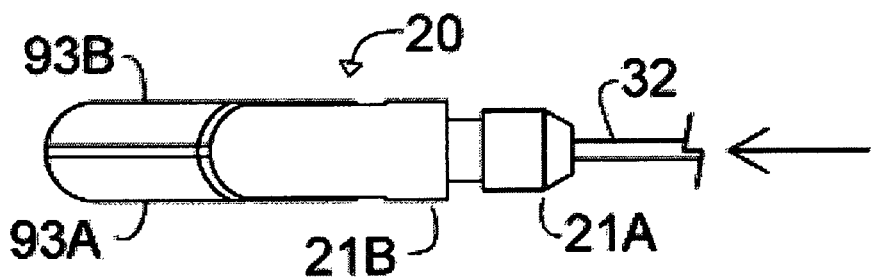
FIG. 21 is a top plan view of the pair of pair of scissors jaws mounted on a jaw retaining body of FIG. 19, showing the jaws in a closed position with the control cable pushing the jaws closed.

In FIGS. 19-21, another alternate pair of jaws 93A and 93B comprises a pair of scissors jaws, the interior edge of each jaw having a full length scissor cutting edge 94A and 94B interacting with a similar scissor cutting edge on the other scissors jaw to cut like scissors, the scissors jaws configured to cut soft tissue and cut suture material.

In FIG. 4, the actuator pin 31 or the drive rod 32 or the drive cable or the drive solid wire extends out of a proximal end opening in the control handle 30A. The means for manually controlling the actuator pin 31 or the drive cable or drive rod or drive solid wire comprise a thumb receiving drive loop 41 attached to a proximal end of the actuator pin 31 or the drive rod 32 or the drive cable or the drive solid wire as one component of a three loop syringe-type configuration 40A. The three loop syringe-type configuration 40A comprises the thumb receiving drive loop 41 and two stationary finger loops 42A and 42B that are rigidly mounted to opposing sides of the handle30A for receiving two fingers of the user, so that the thumb receiving loop 41 receives the force of a user's thumb in the thumb loop to push against the interconnected actuator pin 31 or drive rod 32 or drive cable or drive solid wire and the connected yoke 27 to push the jaws closed while the two fingers that are in the stationary finger loops hold the control handle steady.

The means for locking the jaws 23A and 23B in a closed position to retain collected biopsy tissue within the closed jaws 23A and 23B, or locking the jaws 23A and 23B in a closed position while grasping or manipulating tissue is controlled by the actuator pin 31 engaging with an interior element in the handle.

In FIG. 6 the means for locking the jaws closed is carried out using the actuator pin 31 as described in applicant's U.S. Pat. No. 7,488,296, incorporated herein by reference.

In FIG. 5, the connection structure of the sheath 33 and cable 32 with the jaw assembly 20 is shown. The drive cable 32 or drive rod or drive solid wire, attaches to the yoke body 27 at a proximal end. The drive cable 32 or drive rod or drive solid wire is movably housed within the cable sheath 33 and extends from the yoke 27 in the jaw retaining body 20, shown in FIG. 5, to the control handle 30A or 30B, shown in FIGS. 4 and 6, that is held by a medical professional.

In FIGS. 4 and 6, the control handle 30A and 30B further comprises the actuator pin 31 sliding within the control handle and attached to a proximal end of the drive cable 32 or drive rod or drive solid wire as the means for pushing the drive cable 32 or drive rod or drive solid wire through the cable sheath 33 to close the jaws 23A and 23B, and the means for pulling the drive cable 32 through the cable sheath 33 to open the jaws 23A and 23B. The control handle 30A and 30B further comprises the means for manually controlling the actuator pin 31 attached to the actuator rod and extending outside of the control handle.

In FIG. 6, the actuator pin 31, the drive rod 32, the drive cable, or the drive solid wire extends out of an end opening in the control handle 30B. The means for manually controlling the actuator pin 31 comprises a scissor-type two loop gripping configuration 40B with two rigid arms 44A and 44B each having a finger/thumb receiving loop 43A and 43B at a proximal end. The arms 44A and 44B pivot together at mating pivot point 45 that is spaced apart from the finger/thumb receiving loops 43A and 43B. The first arm 44B is attached to the control handle 30B at a distal end of the first arm 44B and a second arm 44A is attached to a protruding proximal end of the actuator pin 31, drive rod 32, drive cable, or drive solid wire at a distal end of the second arm 44A. This way, pivoting the two loops together with at least one finger in one loop 43A or 43B and a thumb in the other loop 43A or 43B causes the distal end of the second arm 44A to push the connected actuator pin 31 through the control handle 30B which pushes the drive rod 32, drive cable, or drive solid wire and the connected yoke 27 at a distal end to push the jaws 23A and 23B closed.

In using the push-to-close actuated, dual-action, spaced pivot, assembly for jaws, blades, and forceps devices specifically structured for use with a push rod, cable, or solid wire forceps actuator surgical instrument and adapted for a wide variety of types of jaws performing different surgical functions the jaws are engaged by a surgeon holding the control handle to perform a heart tissue biopsy, or other type of tissue biopsy or surgical function on a patient. The jaw device is entered into the patient in the closed jaw position and once the tissue is located, the surgeon engages the handle to pull the actuator pin, thus pulling the drive rod, drive cable, or drive solid wire (housed within the protective sheath) and yoke that is retained within the body of the jaw device and which hooks into and opens the dual-action jaws. The surgeon then engages the control handle to push the actuator pin and the connected drive cable or drive rod or drive solid wire, which in turn pushes against the yoke, closing the jaws simultaneously using maximum jaw force leverage due to two separate fulcrum pivot points on opposite sides of the centerline axis of the jaw body from the distal working ends of the jaws. When the jaws are pushed closed, the surgical function is performed. In the case of the biopsy collecting jaws 23A and 23B, the tissue is cut and contained within the collection bowl formed between the closed jaws, the jaws are locked closed, and then the jaw device removed from the patient to be opened to remove the tissue outside of the patient.

It is understood that the preceding description is given merely by way of illustration and not in limitation of the invention and that various modifications may be made thereto without departing from the spirit of the invention as claimed.

What is claimed is:

1. A push-to-close actuated, dual-action, spaced pivot, assembly for jaws, blades, and forceps devices specifically structured for use with a push-to-close rod, cable, or solid wire forceps actuator surgical instrument and adapted for a wide variety of types of jaws performing different surgical functions, the device comprising:

a jaw retaining body attached to a distal end of a push-to-close rod, cable, or solid wire forceps actuator surgical instrument, the jaw retaining body comprising a jaw receiving platform having a protruding right pivot pin on a first face of the jaw receiving platform spaced apart from a longitudinal center axis of the jaw receiving platform adjacent to a right edge of the jaw receiving platform and a protruding left pivot pin on a second face of the jaw receiving platform spaced apart from the longitudinal center axis of the jaw receiving platform adjacent to a left edge of the jaw receiving platform, thereby providing spaced pivot pins;

two opposing moving jaws, each pivoting about one of the separate spaced pivot pins, each of the jaws comprising one of a pair of push-to-close actuated dual-action spaced pivot jaws on the distal end of the push-to-close rod, cable, or solid wire forceps actuator surgical instrument, so that a left jaw is pivotally connected to the right pivot pin on the jaw retaining body and a right jaw is pivotally connected to the left pivot pin on the jaw retaining body, each of the jaws further comprising an exposed hip on a proximal end of each of the jaws, spaced apart from each of the respective pivot pins, for receiving a pushing force on each of the exposed hips simultaneously to pivot the distal ends of the pair of jaws together for performing a surgical function, the distal ends of the pair of jaws comprising a mating pair of structural elements configured to perform at least one surgical function when the pair of jaws are pivoted together, each of the jaws having a détente adjacent to each of the exposed hips for receiving a pulling force to pull the pair of jaws apart, each of the pair of jaws having a pivot pin opening to receive one of the spaced pivot pins for attaching each of the jaws to the jaw retaining body so that different jaw sets having mating pairs of structured surgical elements to accomplish different surgical functions can be installed by the manufacturer on the same jaw retaining body;

a yoke to open and close the pair of jaws, the yoke being operated by a drive rod, cable, or solid wire from a control handle on a proximal end of the push-to-close rod, cable, or solid wire forceps actuator surgical instrument, the yoke comprising a rigid yoke body attached to the drive rod, cable, or solid wire at a proximal end of the yoke body and two rigid spaced parallel arms rigidly extending from a distal end of the yoke body for operating the jaws, the spaced arms each comprising a pushing end in contact with one of the exposed hips of one of the pair of jaws to enable the pair of arms to push both of the exposed hips of the pair of jaws simultaneously pivoting the distal ends of the pair of jaws together to perform a surgical function, the spaced arms each further comprising a hook to engage one of the détentes of one of the pair of jaws to enable both hooks to pull the détentes simultaneously to pivot the distal ends of the pair of jaws open;

the drive cable, rod, or solid wire comprising a pushing and pulling rod, cable or solid wire movably housed within a cable sheath extending between the jaw retaining body and the control handle, the control handle adapted to be held by a medical professional, the control handle further comprising an actuator rod and a manual control device for controlling the drive rod, cable, or solid wire to push the drive rod, cable, or solid wire to close the jaws and to pull the drive rod, cable, or solid wire to open the jaws.

2. The device of claim 1 wherein the variety of pairs of jaws each having different mating pairs of structured surgical elements configured to perform at least one different surgical function may comprise structured surgical elements taken from the list of structured surgical elements consisting of biopsy collecting elements, biopsy cutting and collecting elements, tissue cutting and removing elements, heart tissue biopsy collecting elements, body tissue biopsy collecting elements, body tissue sample cutting and containing and removing elements, holding elements, positioning elements, manipulating elements, grasping elements, traumatic grasping elements, grasping and manipulating elements, grasping and dissecting elements, atraumatic grasping elements, atraumatic grasping and dissecting elements, atraumatic soft tissue grasping and dissecting elements, soft tissue grasping and manipulation elements, soft tissue grasping and pulling elements, cutting elements, tissue cutting elements, tissue and suture material cutting elements, clamping elements, foreign body grasping elements, surgical elements, jaw elements.

3. The device of claim 1 wherein each of the structured surgical elements of the pair of jaws comprises a biopsy capture bowl for grasping, cutting, and containing biopsy tissue and a surrounding sharp cutting edge for cutting tissue on a distal end to cut and mate with the opposing jaw cutting edge and biopsy capture bowl in a plane aligned with the longitudinal center axis of the jaw receiving platform and perpendicular to the jaw receiving platform of the jaw retaining body to cut and collect biopsy tissue in the combined biopsy capture bowl space, each of the jaws pivotally attached to a separate pivoting pin on the jaw retaining body and each of the jaws pushed together simultaneously by the yoke to cut and collect biopsy tissue and remove it from the body to be studied after releasing the biopsy tissue by having the yoke pull the jaws apart after removal from the body, thereby providing a combined biopsy forceps and grasper instrument jaw device for heart tissue biopsy and general body tissue biopsy.

4. The device of claim 1 wherein the pair of jaws comprises a pair of alligator jaws each jaw comprising a distal end structure having triangular teeth along the length of the distal end interconnecting with a similar array of triangular teeth on the other jaw of the pair of alligator jaws, the interconnecting teeth of the pair of alligator jaws configured for atraumatic grasping and dissecting of delicate soft tissue and alternately for grasping a foreign body.

5. The device of claim 1 wherein the pair of jaws comprises a pair of traumatic grasper jaws each jaw comprising a distal end structure having a partial far end distal array of large isosceles shaped triangular teeth interconnecting with a similar array of large triangular teeth on the far distal end of the other jaw, the traumatic grasper jaws configured to securely grasp and manipulate soft tissue and alternately to grasp a foreign body.

6. The device of claim 1 wherein the pair of jaws comprises a pair of reverse tooth jaws, each jaw having a full array of right triangle shaped teeth having back-facing straight grasping edges perpendicular to the jaw touching an array of tips of a similar array of teeth on the other blade, the reverse tooth jaws configured to securely grasp and manipulate soft tissue and specifically suited for grasping and pulling forces on soft tissue and foreign bodies.

7. The device of claim 1 wherein the pair of jaws comprises a pair of rat tooth jaws each jaw comprising an inwardly and rearwardly pointing cutting hook on a far distal end overlapping with a similar rearwardly facing pointed cutting hook on the other rat tooth jaw, the rat tooth jaws configured to securely grasp, puncture, and manipulate soft tissue and specifically suited for grasping and pulling forces on soft tissue and foreign bodies.

8. The device of claim 1 wherein the pair of jaws comprises a pair of scissors jaws, each jaw having a full length scissor cutting edge interacting with a similar scissor cutting edge on the other scissors jaw to cut like scissors, the scissors jaws configured to cut soft tissue and cut suture material.

9. The device of claim 1 comprising at least one of a drive rod, drive cable or drive solid wire contained within a rigid or flexible cable sheath housing, and further coprising the actuator rod connected to a proximal end of the at least one of the drive rod, drive cable or drive solid wire, the actuator rod sliding axially within the control handle, the manual control device attached to the actuator rod for manually controlling the actuator rod.

10. The device of claim 9 wherein at least one of the actuator rod, the drive rod, the drive cable, or the drive solid wire extends out of a proximal end opening in the control handle and the manual control device comprises a thumb receiving drive loop attached to a proximal end of the actuator rod, the drive rod, the drive cable, or the drive solid wire as one component of a three loop syringe configuration comprising the thumb receiving drive loop and two stationary finger loops rigidly mounted to opposing sides of the handle adapted for receiving two fingers of the user so that the thumb receiving loop is adapted for receiving the force of a user's thumb in the thumb loop to push against the interconnected actuator rod, drive rod, drive cable, or drive solid wire and the connected yoke to push the jaws closed while the stationary finger loops are adapted for receiving the two fingers in the stationary finger loops to hold the control handle steady.

11. The device of claim 3 further comprising a reversible locking mechanism for locking the jaws in a closed position to retain collected biopsy tissue within the closed jaws or locking the jaws in a closed position while grasping or manipulating tissue, the reversible locking mechanism for locking the jaws being controlled by the actuator rod reversibly engaging with an interior element in the handle.

12. The device of claim 9 wherein at least one of the actuator rod, the drive rod, the drive cable, or the drive solid wire extends out of a proximal end opening in the control handle and the manual control device for manually controlling the actuator rod comprises a scissor action two loop gripping configuration comprising two rigid arms each having a finger/thumb receiving loop at a proximal end adapted for receiving a thumb of a user in one loop and a finger of a user in the other loop, the arms pivoted together at mating pivot points spaced apart from the finger/thumb receiving loops and a first arm attached to the control handle at a distal end of the first arm and a second arm attached to a protruding proximal end of the actuator rod, drive rod, drive cable, or drive solid wire at a distal end of the second arm, so that pivoting the two loops together causes the distal end of the second arm to push the connected actuator rod through the control handle to push the drive rod, drive cable, or drive solid wire and the connected yoke at a distal end to push the jaws closed.

\* \* \* \* \*